(12) United States Patent
Dimitrova

(10) Patent No.: US 6,559,156 B1
(45) Date of Patent: May 6, 2003

(54) SUSPENSION CONCENTRATE FORMULATION CONTAINING PYRIMETHANIL

(75) Inventor: Galia Dimitrova, Essex (GB)

(73) Assignee: Bayer Cropscience GmbH (DE)

( * ) Notice: Subject to any disclaimer, the term of this patent is extended or adjusted under 35 U.S.C. 154(b) by 0 days.

(21) Appl. No.: 09/762,775

(22) PCT Filed: Aug. 9, 1999

(86) PCT No.: PCT/GB99/02437

§ 371 (c)(1),
(2), (4) Date: Apr. 6, 2001

(87) PCT Pub. No.: WO00/08931

PCT Pub. Date: Feb. 24, 2000

(30) Foreign Application Priority Data

Aug. 11, 1998  (GB) .............................................. 9817354

(51) Int. Cl.⁷ ....................... A01N 43/54; A61K 31/505
(52) U.S. Cl. ....................................................... 514/275
(58) Field of Search .................................. 514/269, 275

(56) References Cited

U.S. PATENT DOCUMENTS 5,283,231 A   2/1994   Morgan et al.

FOREIGN PATENT DOCUMENTS

DE   4130573   3/1992

OTHER PUBLICATIONS

Bereb et al., Derwent Publication Ltd., London, G.B., Dicloropyrimidinyl Diphenyl Methanol Aqueous Suspension Fungicide Anion Nonionic Surfactant Ethylene Glycol, 1985, Abstract.*

Bristish Crop Protection Concil: The Pesticide Manual, 10th Edition, Clive Tomlin (Ed.), XP002125882, p. 606.*

Derwent Publications Ltd., London, G.B., AN 1985–101264, XP002125883, *Budapesti Vegymuevek:* "Dicloropyrimidinyl Diphenyl Methanol Aqueous Suspension Fungicide Anion Nonionic Surfactant Ethylene Glycol", abstract.

*British Crop Protection Council:* "The Pesticide Manual, 10ᵗʰ Edition", Clive Tomlin (Ed.), Farnham, G.B., XP002125882, see entry No. 607.

* cited by examiner

*Primary Examiner*—Alton Pryor
(74) *Attorney, Agent, or Firm*—Ostrokenk, Faber, Gerb & Soffen, LLP

(57) ABSTRACT

The invention provides an aqueous SC formulation comprising: a) 50 to 80% w/v pyrimethanil; b) 0.2 to 5% w/v of a polyoxyethylene-polyoxypropylene block copolymer surfactant; and c) 0.2 to 5% w/v of a naphthalene formaldehyde condensate surfactant. We have found that formulations according to the invention surprisingly do not solidify when milled during manufacture and also exhibit a low propensity to crystallise when stored for prolonged periods.

18 Claims, No Drawings

SUSPENSION CONCENTRATE FORMULATION CONTAINING PYRIMETHANIL

This application is a 371 of PCT/GB99/02437 filed Jul. 9, 1999.

This invention relates to liquid formulations of pyrimethanil and methods for their preparation. In particular, the invention relates to suspension concentrate (SC) formulations that contain high proportions of solid pyrimethanil.

Commercial SC formulations comprising the fungicide pyrimethanil include Mythos® and Scala®. Typically these formulations contain not more than 40% w/v pyrimethanii. Increasing the amount of pyrimethanil in these formulations above 40% would be advantageous, since it would reduce the cost of transporting a given amount of active ingredient. These savings would be particularly significant where pyrimethanil is transported to remote places where distribution is difficult, such as to tropical zones. However, increasing the concentration of pyrimethanil in these formulation leads to milling problems during manufacture and crystallisation during storage.

It is therefore an object of the invention to devise an SC formulation system containing concentrations of pyrimethanil significantly greater than 40% without experiencing the abovementioned problems.

According to a first aspect, the invention provides an aqueous SC formulation comprising a) 50 to 80% w/v pyrimethanil, preferably 60 to 80% w/v; b) 0.2 to 5% w/v of a polyoxyethylene-polyoxypropylene block copolymer surfactant, preferably 0.3 to 1.5%; and c) 0.2 to 5% w/v of a napthalene formaldehyde condensate surfactant, preferably 0.3 to 1.5%.

We have found that formulations according to the invention surprisingly do not solidify when milled during manufacture and also exhibit a low propensity to crystallise when stored for prolonged periods.

Throughout this specification, unless the context requires otherwise, the word "comprise", or variations such as "comprises" or "comprising" will be understood to imply the inclusion of a stated integer or group of integers, but not the exclusion of any other integer or group of integers including method steps.

Preferably component b) has a molecular weight of 6000 to 14000, especially 9000 to 13000. Further, component b) contains 20 to 80% w/w of polyoxyethylene, especially 40 to 80%. In particular, the molecular weight of component b) is nominally 12000 and the amount of polyoxyethylene is nominally 70% w/w.

Preferably component c) is a salt, particularly the sodium salt.

Preferably the formulation also comprises a dispersant, such as a polymethyl methacrylate-polyethylene glycol graft copolymer, preferably having a molecular weight of 20000 to 30000, in amounts of 1 to 10% w/v, preferably 3 to 8%.

A particularly preferred SC formulation comprises a) approximately 60% w/v pyrimethanil, b) approximately 0.5% w/v of an ethenylenoxy-propyleneoxy block co-polymer surfactant, c) approximately 1% w/v of sodium naphthalene formaldehyde condensate surfactant, d) approximately 5% w/v polymethyl methacrylate-polyethylene glycol graft copolymer, e) approximately 6% w/v propylene glycol and f) approximately 37.5% w/v water.

Our invention is illustrated, by way of example only, with reference to the following.

EXAMPLES

A number of formulations of differing composition were prepared. Table 1 shows the components and their concentrations in w/v. In most cases the components are given as their trade name. Their chemical composition and major function are as follows.

Atlox 4894 is polyoxyethylene alkyl ether (NPE-free); acts as a dispersant and wetter.

Atlox 4913 is polymethyl methacrylate-polyethylene glycol graft copolymer; acts as a dispersant.

Atlox 5406B is a blend of anionic and nonionic surfactants; acts as a dispersant and wetter.

Morwet D425 is sodium naphtalene formaldehyde condensate; acts as a dispersant and viscosity modifier.

Synperonic PE F127 is a polyoxyethylene-polyoxypropylene block copolymer; acts as a dispersant and wetter.

Lauropal X1003 is an ethoxylated alcohol; acts as a wetter.

Polyfon H is sodium lignosulphonate; acts as a dispersant.

Tegopren 5840 is a copolymer consisting of polymethyl siloxanes and polyoxyethylene-polyoxypropylene segments; acts as a wetter.

Reax 85A is sodium lignosulphonate; acts as a dispersant.

Surfynol 104-E is tetramethyl decynediol and ethylene glycol; acts mainly as a wetter.

Surfynol 420 is polyoxyethylene (1.3 moles) tetramethyl decynediol; acts as a wetter.

Arylan SBC25 is sodium dodecylbenzene sulphonate; acts as a wetter.

Witconol NS 500 LQ is a nonionic surfactant blend; acts as a dispersant.

Synperonic 91/6 is polyoxyethylene (6 moles) synthetic primary $C_9/C_{11}$ alcohol; acts as a wetter.

Emcol CC9E is polypropylene glycol (9 moles) diethylmonium chloride; acts as a dispersant and viscosity modifier.

Aerosol OT/S is dioctyl sodium sulfosuccinate; acts as a wetter.

Each Formulation was Prepared as Follows.

Method

All components (except aqueous Kelzan pregel) are dispersed using a high speed mixer. The dispersion is passed through a bead mill under such conditions to achieve the desired particle size distribution and viscosity. Aqueous Kelzan pregel is added to the milled suspension.

Formulations 1 and 2 are formulations of the invention. The remaining formulations are by way of comparison. Each formulation was analysed in terms of milling performance and extent of crystallisation after 2 weeks storage at 54° C. The results are as follows Milling Performance Formulations 3 to 6, 13 to 18, 20 and 24 solidified during milling.

Formulations 1, 2, 7 to 12, 19, 21, 22 and 23 exhibited no milling problems.

Extent of Crystallisation After Storage at 54° C.

Formulations 7 to 12, 19, 21, 22 and 23 exhibited crystal growth after 2 weeks at 54° C., this was particularly marked with 11, 19, 21 and 23.

Formulation 2 showed very slight crystallisation.

Formulation 1 showed no crystal growth.

TABLE 1

| Formulation number | 1 | 2 | 3 | 4 | 5 | 6 | 7 | 8 | 9 | 10 | 11 | 12 |
|---|---|---|---|---|---|---|---|---|---|---|---|---|
| Pyrimethanil (99%) | 606 | 606 | 606 | 606 | 606 | 606 | 606 | 606 | 606 | 606 | 606 | 606 |
| Propylene glycol | 60 | 60 | 60 | 60 | 60 | 60 | 60 | 60 | 60 | 60 | 60 | 60 |
| DC 1520 antifoam | 1 | 1 | 1 | 1 | 1 | 1 | 1 | 1 | 1 | 1 | 1 | 1 |
| Kelzan | 1 | 1 | 1 | 1 | 1 | 1 | 1 | 1 | 1 | 1 | 1 | 1 |
| Proxel XL2 | 1 | 1 | 1 | 1 | 1 | 1 | 1 | 1 | 1 | 1 | 1 | 1 |
| Atlox 4913 | 50 | 50 | 50 | 50 | 50 | 50 | 50 | 50 | 50 | 50 | 50 | 50 |
| Tegopren 5840 | — | — | 15 | — | — | — | — | — | — | — | — | — |
| Reax 85 A | — | — | — | 15 | — | — | — | — | — | — | — | — |
| Surfynol 104-E | — | — | — | — | 15 | — | — | — | — | — | — | — |
| Surfynol 420 | — | — | — | — | — | 15 | — | — | — | — | — | — |
| Morwet D425 | 10 | 5 | — | — | — | — | — | — | — | — | — | — |
| Synperonic PE F127 | 5 | 10 | — | — | — | — | 10 | 10 | 5 | — | — | — |
| Arylan SBC 25 | — | — | — | — | — | — | — | — | — | 15 | — | — |
| Witconol NS 500 LQ | — | — | — | — | — | — | — | — | — | — | 15 | — |
| Emcol CC 9E | — | — | — | — | — | — | — | 1 | — | — | 1 | — |
| Aerosol OT/S | — | — | — | — | — | — | — | — | — | — | — | 15 |
| Atlox 4894 | — | — | — | — | — | — | — | — | — | — | — | — |
| Atlox 5406B | — | — | — | — | — | — | — | — | — | — | — | — |
| Lauropal X1003 | — | — | — | — | — | — | — | — | — | — | — | — |
| Polyfon H | — | — | — | — | — | — | — | — | — | — | — | — |
| Synperonic 91/6 | — | — | — | — | — | — | — | — | — | — | — | — |
| Water | 366 | 366 | 366 | 366 | 366 | 366 | 371 | 370 | 376 | 366 | 365 | 366 |

| Formulation number | 13 | 14 | 15 | 16 | 17 | 18 | 19 | 20 | 21 | 22 | 23 | 24 |
|---|---|---|---|---|---|---|---|---|---|---|---|---|
| Pyrimethanil (99%) | 606 | 606 | 606 | 606 | 606 | 606 | 606 | 606 | 606 | 606 | 606 | 606 |
| Propylene glycol | 60 | 60 | 60 | 60 | 60 | 60 | 60 | 60 | 60 | 60 | 60 | 60 |
| DC 1520 antifoam | 1 | 1 | 1 | 1 | 1 | 1 | 1 | 1 | 1 | 1 | 1 | 1 |
| Kelzan | 1 | 1 | 1 | 1 | 1 | 1 | 1 | 1 | 1 | 1 | 1 | 1 |
| Proxel XL2 | 1 | 1 | 1 | 1 | 1 | 1 | 1 | 1 | 1 | 1 | 1 | 1 |
| Atlox 4913 | — | 20 | — | 10 | 30 | 50 | 20 | 50 | 50 | 50 | 50 | 50 |
| Tegopren 5840 | — | — | — | — | — | — | — | — | — | — | — | — |
| Reax 85 A | — | — | — | — | — | — | — | — | — | — | — | — |
| Surfynol 104-E | — | — | — | — | — | — | — | — | — | — | — | 7.5 |
| Surfynol 420 | — | — | — | — | — | — | — | — | — | — | — | 7.5 |
| Morwet D425 | — | — | — | — | — | — | 15 | 15 | — | — | — | — |
| Synperonic PE F127 | — | — | — | — | — | — | — | — | — | 15 | — | — |
| Arylan SBC 25 | — | — | — | — | — | — | — | — | — | — | — | — |
| Witconol NS 500 LQ | — | — | — | — | — | — | — | — | — | — | — | — |
| Emcol CC 9E | — | — | — | — | — | — | — | — | — | — | — | — |
| Aerosol OT/S | — | — | — | — | — | — | — | — | — | — | — | — |
| Atlox 4894 | 50 | 30 | — | 30 | — | — | 50 | — | — | — | — | — |
| Atlox 5406B | — | — | 50 | 10 | 20 | — | — | — | — | — | — | — |
| Lauropal X1003 | — | — | — | — | — | — | — | — | 15 | — | — | — |
| Polyfon H | — | — | — | — | — | — | — | — | — | — | 15 | — |
| Synperonic 91/6 | — | — | — | — | — | 15 | — | — | — | — | — | — |
| Water | 381 | 381 | 381 | 381 | 381 | 366 | 346 | 366 | 366 | 366 | 366 | 366 |

What is claimed is:

1. An aqueous SC formulation comprising a) 50 to 80% w/v pyrimethanil, b) 0.2 to 5% w/v of a polyoxyethylene-polyoxypropylene block copolymer surfactant, and c) 0.2 to 5% w/v of a napthalene formaldehyde condensate surfactant.

2. A formulation according to claim 1 wherein component b) has a molecular weight of 6,000 to 14,000.

3. A formulation according to claim 1 wherein component b) has a molecular weight of 9,000 to 13,000.

4. A formulation -according to claim 1 wherein component b) contains 20 to 80% w/w of polyoxyethylene.

5. A formulation according to claim 1 wherein component b) contains 40 to 80% w/w of polyoxyethylene.

6. A formulation according to claim 1 wherein the molecular weight of component b) is about 12000 and the amount of polyoxyethylene is about 70% w/w.

7. A formulation according to any preceding claim 1 wherein component c) is a salt.

8. A formulation according to claim 1 which further comprises a polymethyl methacrylate-polyethylene glycol graft copolymer dispersant.

9. A formulation according to claim 8 wherein the dispersant has a molecular weight of 20,000 to 30,000, and is present in an amount of 1 to 10% w/v.

10. A formulation according to claim 1 comprising a) 60 to 80% w/v pyrimethanil, b) 0.3 to 1.5 w/v of a polyoxyethylene-polyoxpropylene block copolymer surfactant, and c) 0.3 to 1.5 w/v of a napthalene formaldehyde condensate surfactant.

11. A formulation according to claim 10 wherein component b) has a molecular weight of 6,000 to 14,000 and contains 20 to 80% w/w of polyoxyethylene.

12. A formulation according to claim 11 wherein component b) has a molecular weight of 9,000 to 13,000 and contains 40 to 80% w/w of polyoxyethylene.

13. A formulation according to claim 12 wherein component c) is a salt.

14. A formulation according to claim 12 which further comprises a polymethyl methacrylate-polyethylene glycol graft copolymer dispersant.

15. A formation according to claim 14 wherein the dispersant has a molecular weight of 20,000 to 30,000, and is present in an amount of 1 to 10% w/v.

16. A formulation according to claim 15 comprising a) approximately 60% w/v pyrimethanil, b) approximately 0.5% w/v of an ethenylenoxy-propyleneoxy block co-polymer surfactant, c) approximately 1% w/v of sodium naphthalene formaldehyde condensate surfactant, d) approximately 5% w/v polymethyl methacrylate-polyethylene glycol graft copolymer, e) approximately 6% w/v propylene glycol and f) approximately 37.5% w/v water.

17. A formulation according to claim 16 wherein the molecular weight of component b) is nominally 12,000 and the amount of polyoxyethylene is nominally 70% w/w.

18. A formulation comprising a) approximately 60% w/v pyrimethanil, b) approximately 0.5% w/v of an ethenylenoxy-propyleneoxy block co-polymer surfactant, c) approximately 1% w/v of sodium naphthalene formaldehyde condensate surfactant, d) approximately 5% w/v polymethyl methacrylate-polyethylene glycol graft copolymer, e) approximately 6% w/v propylene glycol and f) approximately 37.5% w/v water.

* * * * *